Figure 1B:
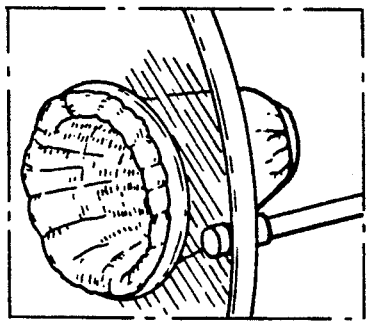
Figure 1D:
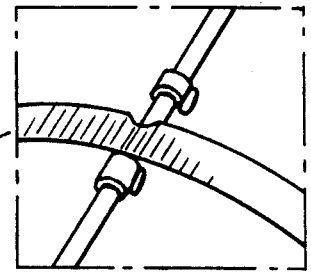
Figure 1A:
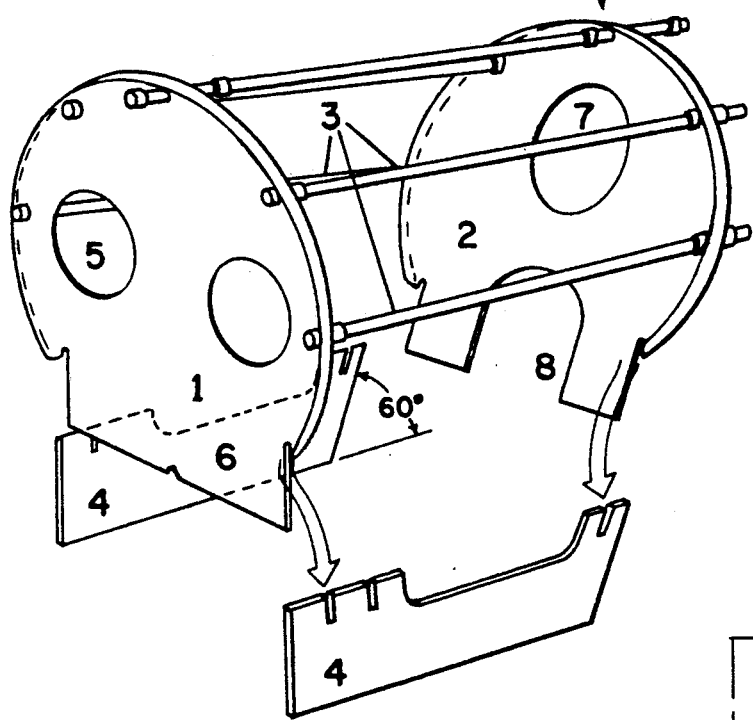
Figure 1C:
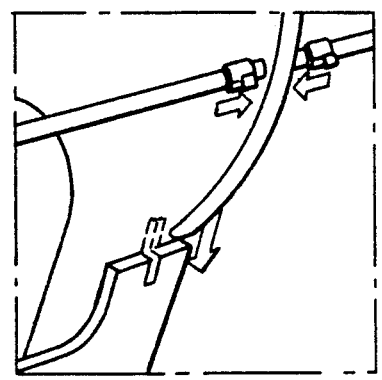

United States Patent [19]

Towfighi et al.

[11] Patent Number: 5,019,031
[45] Date of Patent: May 28, 1991

[54] PROTECTIVE DEVICE FOR PERFORMING CRANIAL AUTOPSIES

[75] Inventors: Javad Towfighi, Hershey; Allan F. Roberts, Mechanicsburg; Norman E. Foster, Camp Hill; Arthur B. Abt, Hershey, all of Pa.

[73] Assignee: The Pennsylvania Research Corporation, University Park, Pa.

[21] Appl. No.: 491,365

[22] Filed: Mar. 9, 1990

[51] Int. Cl.⁵ .................. A61G 10/00; A61G 13/00
[52] U.S. Cl. ........................................ 600/21; 128/846
[58] Field of Search ............................... 128/849–857, 128/863, 847; 606/130; 600/21

[56] References Cited

U.S. PATENT DOCUMENTS

| | | | |
|---|---|---|---|
| 3,490,443 | 1/1970 | DeCupper | 600/21 X |
| 4,224,936 | 9/1980 | Cox | 600/21 |
| 4,296,882 | 5/1990 | Lawrence | 128/850 |
| 4,335,712 | 6/1982 | Trexler | 600/21 |
| 4,876,773 | 10/1989 | Wade | 600/21 X |
| 4,936,318 | 6/1990 | Schoolman | 128/847 |

*Primary Examiner*—Robert A. Hafer
*Assistant Examiner*—Kerry Owens
*Attorney, Agent, or Firm*—Thomas J. Monahan

[57] ABSTRACT

An apparatus and method of use thereof for performing autopsies is described. The invention is particularly useful as a protective device for the prevention of possible transmission of communicable diseases associated with autopsies and includes reusable and disposable components.

3 Claims, 2 Drawing Sheets

PROTECTIVE DEVICE FOR PERFORMING CRANIAL AUTOPSIES

The present invention relates to an enclosure system for providing an environment in isolation from the external environment. The system is concerned particularly, but not exclusively, with an enclosure for isolating cadavers being subjected to cranial autopsies where such cadavers may be associated with viral, bacterial or other infectious agents and it is desireous to contain such agents thereby avoiding the possibility of disease transmission to attending personnel.

By way of background, one of the major problems in performing cranial autopsies in patients with infectious diseases is the aerosolization of particulate material containing the infectious agent when opening the cranial vault. This has greatly contributed to the reluctance of pathologists and autopsy room personnel to perform cranial autopsies, particularly in cases of the acquired immune deficiency syndrome, hepatitis, and Creutzfeldt-Jakob disease. In order to resolve this problem, various precautionary measures, including the use of protective devices during necropsy, have been proposed. [(Centers for Disease Control: Acquired immunodeficiency syndrome (AIDS): Precautions for health-care workers and allied professionals. Ohio Med. 83:776-777, 1987.); (Gajdusek, D. C., Gibbs, C. J., Asher, D. M., et al.: Precautions in medical care of, and in handling materials from, patients with transmissible virus dementia (Creutzfeldt-Jakob disease). N. Engl. J. Med. 297:1253-1258, 1977.); (MacArthur, S., Jacobson, R., Marrero, H., et al.: Autopsy removal of the brain in AIDS: A new technique. HUM. PATHOL. 17:1296-1297, 1986.); (MacArthur, S., Schneiderman, H.: Infection control and the autopsy of persons with human immunodificiency virus. Am. J. Infect. Control 15:172-177, 1987.); (Trexler, P. C., Gilmour, A. M.: Use of flexible plastic film isolators in performing potentially hazardous necropsies. J. Clin. Pathol. 36:527-529, 1983.] Trexler and Gilmour [Trexler, P. C., Gilmour, A. M.: Use of flexible plastic film isolators in performing potentially hazardous necropsies. J. Clin. Pathol. 36:527-529, 1983.] have suggested the use of flexible plastic film isolators over the cadaver's entire body. This method is quite effective in containing the infectious agent; however, it has not gained a wide use due to the high cost and complexity. MacArthur, et al., [(MacArthur S., Jacobson R., Marrero H., et al.: Autopsy removal of the brain in AIDS: A new technique. HUM. PATHOL. 17:1296-1297, 1986.); (MacArthur S., Schneiderman H.,: Infection control and the autopsy of persons with human immunodificiency virus. Am. J. Infect. Control 15:172-177, 1987.)] have avoided this problem by using a clear plastic bag over the cadaver's head during the cutting of the skull. The method is simple and cost-effective, but its major drawback is the lack of a rigid supporting frame which results in the collapse of the bag over the skull and the cutting instrument.

In light of the foregoing summary of some demands and limitations of conventional methods and apparatuses for protection during autopsies and the like, improved devices or methods for providing such protection are highly desirable. An object of this invention is to provide new and useful devices and methods of use for protection against disease transmission during autopsies, particularly cranial autopsies. A further object is to provide a protective tent of clear rigid plastic or other material and transparent polyethylene or other plastic or plastic-like film. An additional object is to provide a device which is simple to use, can be sterilized and re-used with facility, and is easy to store. These and further objects are manifest in the following description and particularly delineated in the appended claims.

Figure 2:
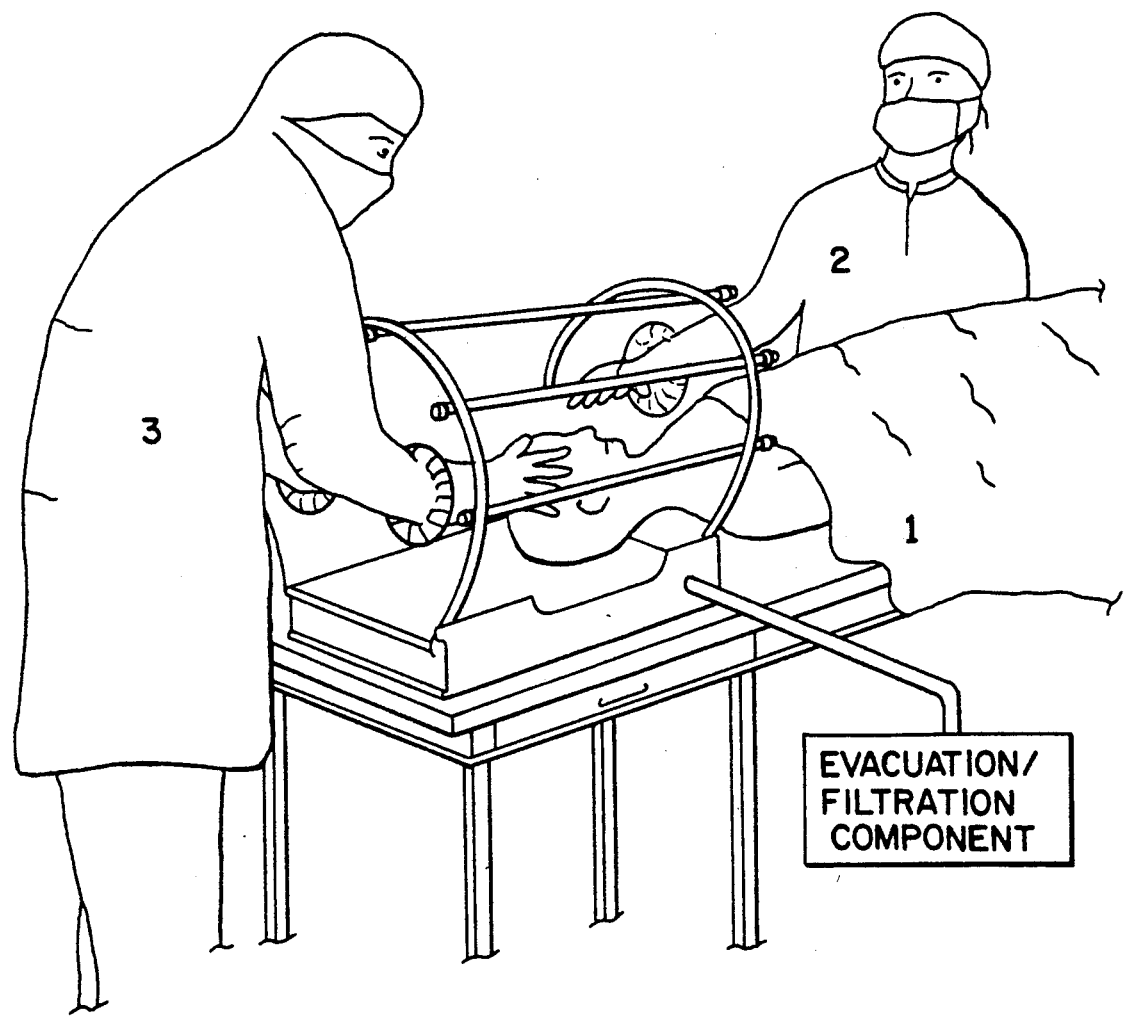

According to the present invention there is the disclosure of a tent consisting of permanent (reusable) and disposable parts. The permanent part consists of four interlocking pieces of clear plastic strengthened by five plastic spacer rods fastened by plastic rings and nylon screws. Embodiments of the invention will now be described with reference to the accompanying drawings in which:

FIGS. 1(a) to 1(d) are diagrammatic representations of a preferred embodiment of the invention showing a protective tent frame;

FIG. 2 is diagrammatic representation of a protective tent positioned over the head and neck of a body being subjected to a cranial autopsy.

Referring firstly to FIG. 1, there is described a protective tent frame with a head shield (1) and a neck shield (2) interlocked with two side shields (4) and connected by five rods (3). The head shield (1) is vertical, has two circular windows (5) for the prosector's arms, and has a small notch (6) at the base for an electric saw cord. The neck shield is tilted, has a circular window (7) for the assistant's arm, and has an opening (8) at the base for the neck. FIG. 1(b) shows details of a window and sleeve. FIG. 1(c) shows details of interlocking neck (2) and side shields (4) and connecting rods (3) secured to the neck shield (2) with rings and screws. Note that the screws are to the side of rings [FIG. 1(d)] and that there is a notch in the strip over the top rod [FIG. 1(d)]. The head and neck pieces (shields) are preferably about ¼ inch thick and are broadened at the edge by the addition of a strip of plastic that is about ⅛ inch thick and about 1 inch wide. These two strips facilitate the application of the disposable film (for example, clear low-density polyethylene stretch film) over the plastic frame. The wide circular windows in the head and neck shields are equipped with permanent plastic rings that support disposable sleeves. The sleeves may be used as iris ports. The head and neck shields are locked into two side plastic pieces, each ½ inch thick. The position of the head shield is vertical, while the neck shield is at about a 60° angle with the side pieces. Referring to FIG. 2, the protection tent is positioned over the head of a body (1) being autopsied. The assistant (2) holds the head in the desired position while the prosector (3) incises the skull. This angle facilitates the positioning of the neck shield over the shoulders.

The unit can be quickly assembled. The covering of transparent polyethylene film readily adheres to the plastic shields to provide an enclosed tent. The two windows in the head shield are used by the prosector for easy handling of the electric saw. The single window in the neck shield is for the assistant's hand, which will help support the cadaver's head in the desired position (FIG. 2). The length of the unit is adjusted in two different positions by moving the head shield. The scalp should be cut and deflected, and the skull area to be cut may be appropriately marked before the positioning of the tent over the head. The opening between the neck and the shield may be covered with a towel soaked with a disinfectant solution. The brain may be taken out under the tent or after the tent has been removed. In the latter case, the prosector should wait approximately five minutes following the craniotomy before removing the tent; this will allow time for the particulate material to settle.

After completion of the autopsy, the reusable parts of the tent can be disassembled, sterilized in a shallow pan containing a disinfectant solution (e.g., 5% sodium hypochlorite further diluted ten times with water), washed, and stored. Special care should be taken in handling the plastic shields in order to avoid scrape marks on the surface. In this regard, the use of a durable, scrape-resistant plastic, such as polycarbonate, is recommended. The potentially contaminated polyethylene film and the sleeves should be disposed of in an appropriate manner. It is also recommended to practice using the tent in routine autopsies before its application in known infectious cases.

Optionally, filtration and/or evacuation devices may be attached to the invention to treat the interior contained environment.

Thus, while we have illustrated and described the preferred embodiment of our invention, it is to be understood that this invention is capable of variation and modification, and we, therefore, do not wish or intend to be limited to the precise terms set forth, but desire and intend to avail ourselves of such changes and alterations which may be made for adapting the invention of the present invention to various usages and conditions. Accordingly, such changes and alterations are properly intended to be within the full range of equivalents and, therefore, within the purview of the following claims. The terms and expressions which have been employed in the foregoing specification are used therein as terms of description and not of limitation, and thus there is no intention in the use of such terms and expressions of excluding equivalents of features shown and described or portions thereof, it being recognized that the scope of the invention is defined and limited only by the claims which follow.

Having thus described our invention and the manner and process of making and using it in such full, clear, concise, and exact terms so as to enable any person skilled in the art to which it pertains, or to with which it is most nearly connected, to make and use the same.

What is claimed is:

1. A protective autopsy apparatus for providing
   a contained environment separate from the ambient environment to maintain enclosed, infectious agents emanating from an opened cranium, comprising:
   a pair of rigid end members, one of which is vertical and the other of which is tilted, wherein the vertical member has at least two circular windows and the tilted member at least one circular window, each said window provided with a disposable, flexible sleeve, said tilted member having an opening for slidably engaging the neck or chest of an autopsy subject;
   multiple connecting elements for connecting and supporting the rigid end members and forming a frame; and
   a flexible, stretchable, disposable, clear film over the frame of the connecting elements, whereby an autopsy subject's head is completely enclosed within said contained environment.

2. The apparatus according to claim 1 wherein a filtration or evacuation component for removing the contained environment is attached to said contained environment.

3. The apparatus according to claim 1 further comprising:
   a pair of side shields having slots formed therein to receive and position said rigid end members in said vertical and tilted positions.

* * * * *